United States Patent [19]

Yodice et al.

[11] Patent Number: 5,178,782

[45] Date of Patent: Jan. 12, 1993

[54] METAL SALTS OF MIXED AROMATIC/ALIPHATIC PHOSPHORODITHIOIC ACIDS

[75] Inventors: Richard Yodice, Willoughby; Allan C. Clark, Mentor, both of Ohio

[73] Assignee: The Lubrizol Corporation, Wickliffe, Ohio

[21] Appl. No.: 856,886

[22] Filed: Mar. 24, 1992

Related U.S. Application Data

[63] Continuation of Ser. No. 784,117, Oct. 30, 1991, abandoned, which is a continuation of Ser. No. 346,883, May 3, 1989, abandoned, which is a continuation of Ser. No. 727,994, Apr. 29, 1985, abandoned, which is a continuation-in-part of Ser. No. 710,829, Mar. 12, 1985, abandoned.

[51] Int. Cl.$^5$ .................................. C10M 137/06
[52] U.S. Cl. .................................. 252/32.7 E
[58] Field of Search .................................. 252/32.7 E

[56] References Cited

U.S. PATENT DOCUMENTS

| | | | |
|---|---|---|---|
| 2,344,393 | 3/1944 | Cook et al. | 252/37 |
| 2,480,673 | 8/1949 | Reiff et al. | 252/32.7 |
| 2,552,570 | 5/1951 | NcNab et al. | 252/32.7 |
| 3,000,822 | 9/1961 | Higgins et al. | 252/32.7 |
| 3,190,833 | 6/1965 | Rhodes | 252/32.7 |
| 3,306,908 | 2/1967 | Le Seur | 260/326.3 |
| 3,318,808 | 5/1967 | Plemich et al. | 252/32.7 |
| 3,346,493 | 10/1967 | Le Suer | 252/32.5 |
| 3,352,949 | 11/1967 | Kawahara et al. | 260/96.4 |
| 3,361,668 | 1/1968 | Wiese | 252/32.7 |
| 3,736,110 | 5/1973 | Owston et al. | 44/56 |
| 3,843,530 | 10/1974 | Niedzielski | 252/32.7 E |
| 3,857,791 | 12/1974 | Marcellis et al. | 252/51.5 A |
| 3,929,653 | 12/1975 | Elliott et al. | 252/46.7 |
| 4,085,053 | 4/1978 | Caspari | 252/32.7 E |
| 4,105,571 | 8/1978 | Shaub et al. | 252/32.7 E |
| 4,113,634 | 9/1978 | Sabol et al. | 252/32.7 E |
| 4,116,871 | 9/1978 | Abbott et al. | 252/32.7 |
| 4,306,984 | 12/1981 | Yamaguchi | 252/46.7 |
| 4,397,791 | 8/1983 | Krause et al. | 252/32.7 |
| 4,466,895 | 8/1984 | Schroeck | 252/32.7 E |

FOREIGN PATENT DOCUMENTS

| | | |
|---|---|---|
| 0024146 | 2/1981 | European Pat. Off. . |
| 0036485 | 9/1981 | European Pat. Off. . |
| 1575670 | 6/1969 | France .................. 252/32.7 R |
| 75578 | 11/1980 | Romania . |
| 0596570 | 1/1948 | United Kingdom .......... 252/32.7 R |
| 0866502 | 4/1961 | United Kingdom .......... 252/32.7 R |

OTHER PUBLICATIONS

Liston et al, American Chemical Society, Sep. 7–12, 1969.

Pless et al, Society of Automotive Engineers, Feb. 28–Mar. 4, 1977.

International Search Report for International Application PCT/US86/00920.

*Primary Examiner*—Jacqueline Howard
*Attorney, Agent, or Firm*—John H. Engelmann; David M. Shold

[57] ABSTRACT

A mixture of metal salts of aromatic/aliphatic phosphorodithioic acids is disclosed. The metal salts, a mixture of the aromatic/aliphatic phosphorodithioic acids contain an aliphatic group and an aromatic group, optionally (H) aliphatic groups, and optionally (B) aromatic groups. The (B) aromatic component can be made utilizing phenol and/or mixtures of cresylic acids. The metal salts are oil-soluble and are useful as corrosion inhibitors and anti-wear agents, particularly in lubricating oil compositions.

7 Claims, No Drawings

METAL SALTS OF MIXED AROMATIC/ALIPHATIC PHOSPHORODITHIOIC ACIDS

CROSS REFERENCE

This is a continuation of application Ser. No. 07/784,117, filed Oct. 30, 1991, which is a continuation of application Ser. No 07,346,883, filed May 3, 1989, which is a continuation of Ser. No. 06/727,994, filed Apr. 29, 1985, which is a continuation-in-part of Ser. No. 06/710,829, filed Mar. 12, 1985 all now abandoned.

BACKGROUND OF THE INVENTION

The present invention relates to one or more metal salts containing a mixture of aromatic and/or aliphatic phosphorodithioic acids. More specifically, the present invention relates to such metal salts which are oil-soluble and can be employed in the lubrication of at least internal combustion engines.

Metal salts of phosphorodithioic acids have been utilized as lubricant additives for inhibiting corrosion and oxidation as well as improving extreme pressure and anti-wear properties.

Various phosphorodithioic acids and their derivatives are known.

Romanian Patent 75,578 relates to bis($C_{3-20}$ alkylphenyl) phosphorodithioates and to zinc salts thereof.

Chem. Abstract 102:81334m (Issue 6, 1985) relates to the distribution of products of $P_2S_5$ with alcohols.

European Patent Application 0,024,146 relates to zinc dihydrocarbyl dithiophosphates wherein the hydrocarbyl compound includes alkyl, alkenyl, aryl, aralkyl, alkaryl and cycloaliphatic groups. These compounds are utilized in combination with copper containing lubricants.

A paper presented at the Sep. 7-12, 1969, American Chemical Society, Division of Petroleum Chemistry, Inc., meeting at New York City, by Liston et al of Chevron Corporation, relates to various types of dihydrocarbon phosphorodithioic acids and salts thereof. The alcohols utilized in making the salts can have at least two carbon atoms and generally five or more.

A paper presented at the S.A.E., Feb. 28–Mar. 4, 1977, Detroit meeting by Pless and Rodgers "Cam and Lifter Wear as Affected by Engine Oil ZDP Concentration and Type" relates to protection from excess wear by predominately alkyl ZDP instead of aryl ZDP.

U.S. Pat. No. 2,344,393 to Cook relates to metal dithiophosphates having one or more long chain alkyl groups to render them sufficiently soluble in lubricating oils. Moreover, it recognized that the zinc salt of diamylphosphorodithioic acid was oil-soluble.

U.S. Pat. No. 2,480,673 to Reiff relates to reacting a hydroxyaromatic compound with $P_2S_5$ and thereafter treating the product with finely divided zinc. The amount of zinc utilized, however, was small and related to removing impurities as generally opposed to forming a salt.

U.S. Pat. No. 2,552,570 to McNab relates to dihydrocarbyl phosphorodithioic acids wherein the hydrocarbon group can be either aliphatic or aromatic and contain a total of 10 carbon atoms in the combined aliphatic groups, whether or not attached to an aromatic nucleus.

U.S. Pat. No. 3,000,822 to Higgins relates to zinc salts of a mixture of dialkyl phosphorodithioic acids wherein the alkyl groups comprise a mixture of lower molecular weight primary aliphatic hydrocarbon radicals having less than five carbon atoms and higher molecular weight primary aliphatic hydrocarbon radicals having at least five carbon atoms.

U.S. Pat. No. 3,190,833 to Rhodes relates to oil-soluble metal phosphorodithioates which contain a total of at least 7.6 aliphatic carbon atoms per atom of phosphorus. To improve the oil-solubility of the metal salts, they are reacted with up to about 0.75 mole of an epoxide.

U.S. Pat. No. 3,306,908 to LeSuer relates to Group II metal phosphorodithioates having substantially hydrocarbon radicals.

U.S. Pat. No. 3,318,808 to Plemich discloses that higher carbon containing alkyl groups of above four carbon atoms enhance oil-solubility. The patent also teaches the combination of $C_4$ and lower primary and/or secondary alcohols with $C_5$ and above alcohols.

U.S. Pat. No. 3,346,493 to LeSuer also relates to Group II metal hydrocarbon phosphorodithioates.

U.S. Pat. No. 3,352,949 to Kawahara relates to certain thioesters of dithiophosphoric acid as motor fuel additives.

U.S. Pat. No. 3,361,668 to Weise relates to a process for preparing an O,O'-diester of phosphorodithioic acid by reacting phosphorus pentasulfide with a mixture of a monohydroxy alcohol or phenol and an alkyl amine, cycloalkylamine or heterocyclic amine.

U.S. Pat. No. 3,736,110 to Ownston relates to rust-inhibitors and more particularly to organic imidazoline salts of mono- and dicresylic phosphates.

U.S. Pat. No. 3,843,530 to Niedzielski relates to preparing non-crystalline mixtures of basic or mixed basic and neutral zinc salts of dialkyldithiophosphates containing from 1 to 13 carbon atoms in the alkyl group. The mixtures of the zinc salts contain from 4 to 13 different alkyl groups, have an average carbon content of 3.5 to 4.5, and contain at least 12% by weight of zinc.

U.S. Pat. No. 3,929,653 to Elliott relates to certain dithiophosphate compounds which are useful as additives. It furthermore relates to a process of reacting a di(organo)dithiophosphoric acid and a monocyclic, non-conjugated olefin containing from 8 to 12 carbon atoms . and at least two ethylenically unsaturated double bonds in the ring, and optionally bearing one or more alkyl, alkoxy or hydroxy groups on the ring.

U.S. Pat. No. 4,085,053 to Caspari relates to a process for manufacturing metal dithiophosphates, and metal dithiophosphate compositions. The alcohol often used is an alkyl alcohol.

U.S. Pat. No. 4,105,571 to Shaub relates to a storage stable lubricating composition having improved anti-wear properties provided by a base oil composition containing an additive combination of (1) a zinc dihydrocarbyl dithiophosphate, (2) an ester of a polycarboxylic acid and a glycol, and (3) an ashless dispersant.

U.S. Pat. No. 4,113,634 to Sabol relates to the manufacture of metal diaryl dithiophosphates by reacting $P_2S_5$ with a hydroxyaryl compound to form a dithiophosphoric acid and neutralizing said acid with metal in the presence of a promoter, said promoter comprising dialkyl dithiophosphoric acid.

U.S. Pat. No. 4,306,984 to Yamaguchi relates to a procedure for rendering oil insoluble metal $C_2$–$C_3$ dialkyl dithiophosphates oil-soluble by forming a complex between the dithiophosphate and an alkenyl or alkyl mono- or bis-succinimide.

U.S. Pat. No. 4,466,895 to Schroeck relates to certain metal salts of one or more dialkylphosphorodithioic acids wherein the alkyl groups, the total number of carbon atoms per phosphorus atom and the like fall within specific ranges.

SUMMARY OF THE INVENTION

Accordingly, it is an aspect of the present invention to produce metal salts which are oil-soluble.

It is a further aspect of the present invention to provide metal salts, as above, wherein the reaction with the metal or the basic metal compound is carried out at a low temperature to promote the salt formation.

It is another aspect of the present invention to provide metal salts, as above, wherein phenol and/or cresylic acids are utilized.

It is still a further aspect of the present invention to provide a mixture of metal salts, as above, which can function as effective anti-wear agents.

These and other aspects of the present invention will become apparent from the attached specification which fully describes the present invention.

In general, metal salts of aromatic/aliphatic phosphorodithioic acids, comprises: one or more metal salts of a mixture of the aromatic/aliphatic phosphorodithioic acids containing an (H) aliphatic group and (B) aromatic group wherein said aromatic group is phenyl, a low hydrocarbyl arene or mixtures thereof; optionally (H) aliphatic groups, and optionally (B) aromatic groups.

Metal salts comprising: the reaction product of (J) one or more aliphatic alcohol and (D) one or more aromatic alcohol with (E) phosphorus sulfides and optionally sulfur and (F) the subsequent reaction of the product formed thereby with a metal or a basic metal compound.

DESCRIPTION OF THE PREFERRED EMBODIMENTS

In yet another embodiment, discussed hereinbelow, desirably the phosphorodithioic acids have an aliphatic group therein as well as an aromatic group. That is, the alcohols which are reacted with the phosphorous sulfides to form mixtures of the present invention are an aliphatic alcohol and an aromatic alcohol. The result approximates a statistical mixture of phosphorodithioic acids having only aliphatic groups thereon, only aromatic groups, or an aliphatic group and an aromatic group.

The term "hydrocarbyl substituent" or "hydrocarbyl group" is used throughout this specification and in the appended claims to denote a group having a carbon atom directly attached to the remainder of the molecule and having predominately hydrocarbon character within the contex of this invention. Such groups include the following:

(1) Hydrocarbon groups, that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, the two indicated substituents may together form a cyclic group). Such groups are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon groups, that is, groups containing non-hydrocarbon substituents which, in the context of this invention, do not alter predominantly hydrocarbon character of the group. Those skilled in the art will be aware of suitable substituents (e.g., halo, hydroxy, alkoxy, carbalkoxy, nitro, alkylsulfoxy).

(3) Hetero groups; that is, groups which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

The (B) low hydrocarbyl substituted aromatic alcohols generally have a total of 4 or less carbon atoms in the hydrocarbyl substituent. The hydrocarbyl group can generally be any suitable substituent such as aliphatic with an alkyl being preferred. The (B) low hydrocarbyl substituted aromatic alcohol can be represented by the following formula

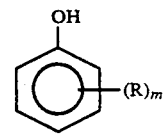

where (R)m can be suitable hydrocarbyl group(s), desirably it is alkyl group(s) having from 0 to 4 carbon atoms, desirably from 1 to 4 carbon atoms with from 1 to 3 carbon atoms being preferred. The number of the R group(s), that is m, is an integer of from 1 to 3 with 1 or 2 being preferred. In the situation where R is 0 carbon atoms, the low hydrocarbyl substituted aromatic alcohol is simply phenol. Phenol is generally not desired in any large amount since it imparts poor solubility to products made therefrom. A general class of compounds falling within the above formulation are generally referred to as the cresylic acids. Such a group of compounds usually contain numerous different (B) low hydrocarbyl substituted aromatic alcohols including the cresols from which the name is derived. Suitable alcohols thus include ortho-cresol, meta-cresol, para-cresol, the various xylenols such as 2,6-xylenol, 2,4-xylenol, 2,5-xylenol, 2,3-xylenol, and 3,4-xylenol. Another group of alcohols are the ortho, meta- and para-ethylphenols. Still another group of alcohols are the propyl substituted phenols. The various trimethyl substituted phenols constitute yet another group with specific examples including 2,3,5-trimethylphenol, 2,3,4-trimethylphenol, 2,4,5-trimethylphenol, 3,4,5-trimethylphenol and the like. An example of low hydrocarbyl substituted aromatic alcohols containing four substituted carbon atoms are the various tetramethylphenols such as 2,3,5,6-tetramethylphenol, 2,3,4,5-tetramethylphenol, 2,3,4,6-tetramethylphenol, and the like. A still further group of such aromatic alcohols include the various ethyl-methylphenols such as 4-ethyl-2-methyl-phenol, 5-ethyl-2-methylphenol and the like. Inasmuch as such aromatic alcohols are derived from various fossil fuels and depend upon the particular type of fossil fuel and/or as well as the region of the world from which they are obtained, or are derived synthetically, the various cresylic acids or the (B) low hydrocarbon content substituted aromatic alcohols can vary greatly in content.

According to the present invention, it is important that the low hydrocarbyl substituent $(R)_m$ contain an overall average of a small number of total carbon atoms. Accordingly, all of the low hydrocarbyl substituents, $(R)_m$, generally contain an overall average number of from about 0 or from about 0.5 to 4 carbon atoms, desirably from about 1.0 to about 3.5 carbon atoms, and preferably from about 2.0 to about 3.0 carbon atoms.

The amount of the low hydrocarbyl substituted aromatic alcohols is generally from about 25 to about 90 percent equivalents, desirably from about 35 to about 90 percent equivalents, and preferably from about 60 to about 85 percent equivalents based upon the total number of equivalents of both the (A) high hydrocarbyl substituted aromatic alcohols and the (B) low hydrocarbyl substituted aromatic alcohols.

Sources of low hydrocarbyl substituted aromatic alcohols or cresylic acids are numerous. A typical example is Product CA-33 from the Merichem Company of Houston, Tex. Such a product has an organic composition as determined by gas chromatograph and is set forth in Table I.

TABLE I

| Compound | Weight % |
|---|---|
| Phenol | 0.1 |
| O-Cresol | Trace |
| 2,6-Xylenol | Trace |
| P-Cresol | 0.2 |
| M-Cresol | 0.6 |
| O-Ethylphenol | 0.3 |
| 2,4-Xylenol | 19.4 |
| 2,5-Xylenol | 19.3 |
| 2,4,6-Trimethyl Phenol | 0.8 |
| 2,3-Xylenol | 8.5 |
| P-Ethylphenol | 10.7 |
| M-Ethylphenol | 23.0 |
| 3,5-Xylenol | 12.0 |
| 3,4-Xylenol | 3.3 |
| $C_3$ Phenols | 1.8 |

The average number of carbon atoms in the hydrocarbyl substituent is approximately 2.07.

Another example of a cresylic acid composition is Product CA-57 of the Merichem Company which according to gas chromatograph has the following analysis as set forth in Table II.

TABLE II

| Compound | Weight % |
|---|---|
| Phenol | — |
| O-Cresol | Trace |
| 2,6-Xylenol | — |
| P-Cresol | 0.1 |
| M-Cresol | 0.2 |
| O-Ethylphenol | Trace |
| 2,4-Xylenol | 1.0 |
| 2,5-Xylenol | 1.2 |
| 2,4,6-Trimethyl Phenol | 0.8 |
| 2,3-Xylenol | 10.7 |
| P-Ethylphenol | 15.3 |
| M-Ethylphenol | 40.5 |
| 3,5-Xylenol | 23.3 |
| 3,4-Xylenol | 4.8 |
| $C_3$ Phenols | 2.1 |

The average number of carbon atoms in the hydrocarbyl substituent ia approximately 2.05.

Yet another example of a commercial cresylic acid is Product XL-85 sold by the Productol Chemical Division of Ferro Corporation, Whittington, Calif. Gas chromatograph analysis revealed the following composition as set forth in Table III.

TABLE III

| Compound | Weight % |
|---|---|
| Phenol | Trace |
| Ortho Cresol | Trace |
| Meta/Para Cresol | 1.0 |
| 2,4-Xylenol Group | 1.0 |
| 3,4-Xylenol Group | 36.0 |
| 3,5-Xylenol Group | 12.0 |
| Higher Phenols | 50.0 |

The average number of carbon atoms in the hydrocarbyl substituent is approximately 2.8.

As should be apparent, there are numerous sources and types of low hydrocarbyl substituted aromatic alcohols which can be utilized in the present invention with regard to the (B) type reactant or component.

According to another embodiment of the present invention, only low hydrocarbyl substituents of the aromatic phosphorodithioic acid are utilized. In other words, no high hydrocarbyl substituents are utilized and hence there is no mixture of metal salts of the aromatic phosphorodithioic acids containing high hydrocarbyl substituents. However, it is essential to the present embodiment that at least two different types of low hydrocarbyl substituents be utilized. That is, it has been found that when different aromatic alcohols are reacted with various types of phosphorus sulfides as well as optional non-phosphorus containing sulfur compounds as set forth below, the result approximates a statistical mixture of aromatic phosphorodithioic acids often having different hydrocarbyl substituents within the same acid or individual molecule. Moreover, such different low hydrocarbyl substituents within the same individual phosphorodithioic acid have unexpectedly been found to impart favorable solubility to such compounds. Such favorable solubility is not contained by metal salts made from a single type of low hydrocarbyl substituted aromatic alcohol. In other words, mixtures of various or different low hydrocarbyl substituted aromatic alcohols are necessary in preparing the metal salts of the present embodiment.

The low hydrocarbyl substituted aromatic alcohols with regard to this embodiment can be the same as the above (B) alcohols. That is, the alcohols can be represented by the formula

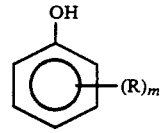

where R is an alkyl group having from 0 or 0.5 to 4 carbon atoms, desirably from 1 to 4 carbon atoms with from 1 to 3.5 or 3 carbon atoms being preferred. The number of such R groups, that is m is an integer from 1 to 3 with 1 or 2 being preferred. Inasmuch as such compounds have been described hereinabove, the description thereof will not be repeated but rather is hereby fully incorporated by reference. However, it is essential that these two different or distinct alcohols be utilized to impart favorable solubility to the metal salt. By the term "different," it is meant that the alcohols are not identical or the same. The term "different" includes not only different structural alcohols, but homologues of a particular aromatic alcohol as well as isomers of the same alcohol. Thus, by way of example meta, ortho and paracresol are different alcohols. Similarly, the various xylenols constitutes a different type of an aromatic alcohol, for example 2,6-xylenol, or 2,4-xylenol, or 3,4-xylenol or the like.

As set forth above, various sources of low hydrocarbyl aromatic alcohols which already contain at least two different types of alcohols therein can be utilized such as the various cresylic acids which are hereby incorporated by reference. The amount of the various types of the low hydrocarbyl substituted aromatic alcohol is such that satisfactory solubility in a diluent oil is obtained.

The acids of the present invention are generally prepared by reacting a solution containing a combination of both the low hydrocarbyl substituted aromatic alcohols as well as the high hydrocarbyl substituted aromatic alcohols, in a ratio as set forth within the above limits, with various types of phosphorus sulfides. When necessary, non-phosphorus containing sulfur compounds can be used. Alternatively, the acids of the present invention are also generally prepared by reacting a solution containing a mixture of different low hydrocarbyl substituted aromatic alcohols, in a ratio as set forth within the above limits, with various types of phosphorus sulfides as well as optional non-phosphorus containing sulfur compounds. Examples of various phosphorus sulfides include $P_2S_3$, $P_2S_5$, $P_4S_3$, $P_4S_7$. Examples of optional sulfur compounds include sulfur and sulfurized olefins. In the preparation of the acids, the phosphorus sulfides are initially reacted with the mixture of high and low hydrocarbyl substituted aromatic alcohols and then optionally reacted with the phosphorus-free sulfur compounds. Similarly, the phosphorus sulfides can be initially reacted with the mixture of solely the low hydrocarbyl substituted aromatic alcohols and then optionally reacted with the phosphorus-free sulfur compounds. In any event, a preferred phosphorus-sulfur compound is phosphorus pentasulfide.

The preparation of the desired phosphorodithioic acids generally involves a reaction of from about 3 to about 5 moles and desirably about 4 moles of the alcohol mixture per mole of phosphorus pentasulfide in an inert atmosphere such as nitrogen. The reaction is generally carried out within a temperature range of from about 50° C. to about 200° C., desirably from about 80° C. to about 200° C. and preferably from about 110° C. to about 140° C. The reaction is normally completed in the time period of from about 1 to 3 hours with hydrogen sulfide being liberated during the reaction.

The metal salts of the hydrocarbyl substituted aromatic phosphorodithioic acids are readily formed by the reaction of the metal or the basic metal compound with the acid. Simply mixing and heating the two reactants together is sufficient to cause the reaction to take place. According to the present invention, it is important that the reaction temperature with regard to the formation of the metal salt be kept low to avoid excessive hydrolysis. Inasmuch as hydrolysis is to be avoided, the reaction temperature is generally from about 30° C. to about 90° C. and preferably from about 50° C. to about 80° C.

Typically, the metal salt formation is carried out in the presence of a diluent oil, a desired oil is a low viscosity (e.g. about 3–7 centistokes @40° C.) naphthenic oil since it gives a fluid product.

Another aspect of the present invention is that at the reaction temperature of the formation of the salt, a promoter is not required. That is, the reaction between the acid and the basic metal compound is free from any promoter. Generally, a metal salt is desired which is neutral or basic and hence, an equivalent or a slight excess of the metal or the basic metal compound is utilized to yield such an end product. Accordingly, the amount of metal or basic metal compound when utilized in an excess is from about 0 to about 20 percent with an excess of from about 5 percent to about 15 percent equivalents being desirable.

Types of metals suitable for the present invention include zinc, copper, nickel, cobalt, iron, manganese, potassium, tin, sodium, calcium especially in combinations with other metals, as well as combinations of any of the previous metals. Additionally, basic metal compounds can be utilized such as various metal oxides, acetates and the like. Thus, examples of specific basic metal compounds include zinc oxide, copper oxide, sodium hydroxide, potassium hydroxide, calcium oxide, zinc acetate, copper acetate, and the like. Examples of preferred metals include copper and zinc with zinc being especially preferred. Examples of preferred basic metal compounds include zinc oxide and copper oxide.

The metal salts of the present invention have been found to impart good anti-wear properties to various organic diluents. Moreover, in view of the fact that aromatic phosphorodithioates typically give poor anti-wear results, the fact that the mixtures of the present invention give good anti-wear results was actually unexpected.

The following examples illustrate the preparation of the phosphorodithioic acids and the metal salts thereof. All parts and percentages are by weight unless otherwise indicated.

EXAMPLE 1A

A mixture of 2945 parts (24 equivalents) of Cresylic Acid 57 and 1152 parts (6.0 equivalents) of heptylphenol is heated to 105° C. under a nitrogen atmosphere whereupon 1665 parts (15 equivalents) of phosphorus pentasulfide are added in portions over a period of 3 hours while maintaining the temperature of the mixture between about 115°–120° C. The mixture is maintained at this temperature for an additional 1.5 hours upon completion of addition of the phosphorus pentasulfide and then cooled to room temperature. The reaction mixture is filtered through a filter aid, and the filtrate is the desired phosphorodithioic acid.

EXAMPLE 1B

Zinc oxide (541 parts, 13.3 equivalents), 14.4 parts (0.24 equivalents) of acetic acid and 1228 parts of mineral oil are charged to a 12 liter flask. A vacuum (100–100 mm) is applied while raising the temperature to about 70° C. The phosphorodithioic acid (4512 parts, 12.0 equivalents) prepared in Example 1A is added over a period of about 5 hours while maintaining the temperature at 68°–72° C. The water is removed as it forms. The temperature is maintained at 68°–72° C. for 2 hours after the addition of phosphorodithioic acid is complete. To ensure complete removal of the water, vacuum is adjusted to about 10 mm and the temperature is raised to about 105° C. and maintained at this temperature for 2 hours. The residue is filtered and the filtrate is the desired product. The product contains 6.26% P (6.09% theory) and 6.84% Zn (6.38% theory).

EXAMPLE 2A

A mixture 432 parts (4 equivalents) p-cresol and 432 parts (4 equivalents) of m-cresol is heated to 110° C. under a nitrogen atmosphere whereupon 444 parts (4 equivalents) of phosphorus pentasulfide are added in portions over a period of 2.5 hours while maintaining the temperature of the mixture at about 110° C. The mixture is maintained at this temperature for an additional 1.5 hours upon completion of the addition of the phosphorus pentasulfide and then cooled to room temperature. The reaction mixture is filtered through a filter aid and the filtrate is the desired phosphorodithioic acid.

EXAMPLE 2B

Zinc oxide (175 parts, 2.2 equivalents) 3.55 parts (0.06 equivalents) of acetic acid, 250 parts of heptane are charged to a 3-liter flask. A vacuum is applied while raising the temperature to about 50° C. The phosphorodithioic acid (1145 parts, 3.5 equivalents) prepared in Example 2A is added over a period of about 2 hours while maintaining the temperature at about 60°-65° C. The temperature is raised to about 80° C. and kept at this temperature for 3 hours. The residue is filtered and the filtrate is the desired product. The product contains 9.01% P (8.59% theory) and 9.11% Zn (9.06% theory).

EXAMPLE 3A

Heptylphenol (1540 parts, 8.0 equivalents) is heated to 125° C. under a nitrogen atmosphere whereupon 444 parts (4.0 equivalents) of phosphorus pentasulfide are added in portions over a period of 1 hour while maintaining the temperature of the mixture at about 145° C. The mixture is held at this temperature for an additional 4 hours upon completion of the addition of the phosphorus pentasulfide and then cooled to room temperature. The reaction mixture is filtered through a filter aid and the filtrate is the desired phosphorodithioic acid.

EXAMPLE 3B

Zinc oxide (90.5 parts, 2.22 equivalents), 2.54 parts (0.04 equivalents) of acetic acid, 2.54 parts of water, and 919 parts of mineral oil are charged to a 3 liter flask. The mixture is heated to about 70° C. and 1000 parts (1.83 equivalents) of the phosphorodithioic acid of Example 3A are added over a period of 1 hour while maintaining the temperature at 70°-75° C. Upon completion of the addition of the phosphorodithioic acid the temperature is maintained at 70°-75° C. for 3 hours. Vacuum is applied and the temperature is raised to about 105° C. The residue is filtered and the filtrate is the desired product. The product is a clear liquid and contains 3.0% P.

EXAMPLE 4A

Dodecyl phenol (2100 parts, 8.0 equivalents) is heated to 125° C. under a nitrogen atmosphere whereupon 444 parts (4.0 equivalents) of phosphorus pentasulfide are added in portions over a period of 1 hour while maintaining the temperature of the mixture at about 145° C. The mixture is held at this temperature for an additional 4 hours upon completion of the addition of the phosphorus pentasulfide and then cooled to room temperature. The reaction mixture is filtered through a filter aid and the filtrate is the desired phosphorodithioic acid.

EXAMPLE 4B

Zinc oxide (90.5 parts, 2.22 equivalents), 2.54 parts (0.04 equivalents) of acetic acid, 2.54 parts of water, and 597 parts of mineral oil are charged to a 3 liter flask. The mixture is heated to about 70° C. and 1271 parts (1.83 equivalents) of the phosphorodithioic acid of example 4A are added over a period of 1 hour while maintaining the temperature at 70°-75° C. Upon completion of the addition of the phosphorodithioic acid the temperature is maintained at 70°-75° C. for 3 hours. Vacuum is applied and the temperature is raised to about 105° C. The residue is filtered and the filtrate is the desired product. The product is a clear liquid and contains 3.2% P.

EXAMPLE 5A

Cresylic Acid 57 (356 parts, 2.9 equivalents) is heated to about 113° C. under a nitrogen atmosphere whereupon 161 parts (1.45 equivalents) of phosphorus pentasulfide are added in portions over a 1.5 hour period while maintaining the temperature at 110°-115° C. The mixture is held at this temperature for an additional 2 hours upon completion of the addition of phosphorus pentasulfide and then cooled to room temperature. The reaction mixture is filtered through a filter aid and the filtrate is the desired phosphorodithioic acid.

EXAMPLE 5B

Zinc oxide (45.1 parts, 1.1 equivalents), 1.2 parts (0.02 equivalents) of acetic acid, and 96.1 parts of mineral oil are charged to a 1 liter flask. A vacuum (about 100 mm) was applied and the temperature was raised to about 70° C. The phosphorodithioic acid (352 parts, 1.0 equivalents) of Example 5A is added over a 2 hour period while maintaining the temperature at 72°-79° C. Water was removed as it formed. Upon completion of the phosphorodithioic acid addition, the temperature is held at 70°-75° C. for an additional 3 hours. The mixture is filtered and the filtrate is the desired product. The product is a clear liquid.

EXAMPLE 9A

A mixture of 241 parts (2.0 equivalents) of Cresylic Acid 33 and 408 parts (2.0 equivalents) of heptylphenol are heated to 90° C. under a nitrogen atmosphere whereupon 222 parts (2.0 equivalents) of phosphorus pentasulfide are added in portions over a 1 hour period. The temperature is allowed to rise to about 120° C. during the addition and is maintained at 115°-120° C. for 2 hours after the addition of phosphorus pentasulfide is complete. The reaction mixture is filtered and the filtrate is the desired phosphorodithioic acid.

EXAMPLE 9B

Zinc oxide (49.2 parts, 1.21 equivalents), 1.2 parts (0.02 equivalents) of acetic acid, and 218 parts of xylene are charged to a 1 liter flask. Vacuum (about 94 mm Hg) is applied and the mixture is heated to about 89° C. The phosphorodithioic acid (442 parts, 1.0 equivalents) prepared in Example 9A is added over a 1 hour period. The temperature is maintained at about 89° C. for 3 hours after the phosphorodithioic acid addition is completed. Mineral oil (118 parts) is added. The vacuum is adjusted to about 10 mm Hg and the temperature is raised to about 100° C. to remove xylene. The residue is filtered and the filtrate is the desired product. The product contains 5.51% P (5.19% theory) and 5.72% Zn (5.44% theory).

EXAMPLE 10A

A mixture of 615 parts (5.0 equivalents) of Cresylic Acid 33 and 355 parts (1.85 equivalents) of heptylphenol is heated to 120° C. under a nitrogen atmosphere. Phosphorus pentasulfide (344 parts, 3.1 equivalents) is added in portions over a 2 hour period while maintaining the temperature of the mixture at about 127°–135° C. The temperature is held at 130° C. for 1.5 hours after the addition of phosphorus pentasulfide is complete and then cooled to room temperature. The reaction mixture is filtered and the filtrate is the desired phosphorodithioic acid.

EXAMPLE 10B

Zinc oxide (112 parts, 2.75 equivalents) and 186 parts of mineral oil are charged to a 2 liter flask. The phosphorodithioic acid (1045 parts, 2.5 equivalents) prepared in Example 10A is added over a 2 hour period while allowing the temperature of the reaction mixture to increase to about 50° C. Upon completion of the phosphorodithioic acid addition, the temperature is increased to and maintained at about 75° C. for 3 hours. Vacuum (about 15 mm Hg) is applied and the temperature of the reaction mixture increased to about 100° C. The residue is filtered and filtrate is the desired product. The product contains 5.98% P (5.93% theory) and 6.79% Zn (6.22% theory).

The products of the various examples, contained in a fully formulated lubricating composition, were then tested with regard to a Timken "OK" load test as well as a contact pressure test in accordance with ASTM D 2782 with the exception that in the "OK" load test the following differences were made:

1. Test cup and block surfaces are merely "wetted" with test lubricant (approximately 5 drops on block). No test sample is recirculated over the surfaces during the test.
2. Test duration is 5 minutes under load.
3. This procedure is run as an "OK" Load test, determining "OK" Load as in ASTM Test D 2782 except utilizing the following load increments:
   a. "OK" Load ≦20 lb.: Determine "OK" Load to the nearest 1 lb.
   b. "OK" Load >20 lbs.: Determine "OK" Load using standard load increments as described in ASTM Test D 2782.

The results of various dithiophosphate salts according to the present invention are set forth in Table IV.

TABLE IV

TIMKEN EVALUATION OF AROMATIC ZINC DITHIOPHOSPHATES AT 0.05% P

| Example | Alkyl Phenol (Mole %) | OK Value (lbs) | Contact Pressure (p.s.i.) |
|---|---|---|---|
| 1B | 80% Cresylic Acid 57 20% Heptylphenol | 20 | 15,325 |
| 2B | 50% p-cresol 50% m-cresol | 25 | 12,700 |
| 3B | 100% Heptylphenol | 13 | 7,750 |
| 4B | 100% Dodecylphenol | 15 | Scoring |
| 9B | 50% Cresylic Acid 33 50% Heptylphenol | 20 | 11,500 |

As apparent from the above table, compositions containing Examples 1B and 9B made according to the present invention utilizing high and low hydrocarbyl substituted aromatic alcohols had good load test "OK" values as well as good contact pressures. However, compositions containing only a high hydrocarbyl substituted aromatic phosphorodithioic acid salt had poor values. Specifically, Example 3B containing heptylphenol had an "OK" value of 13 and a contact pressure of 7,750 psi. Example 4B had an "OK" value of 15 and actually had scoring damage imparted thereto. Example 2B which related to an all low but different low hydrocarbyl substituents in accordance with another embodiment of the present invention had good test results. The solubility was good in fully formulated lubricant compositions.

According to another embodiment of the present invention, an (H) aliphatic alcohol and a (B) aromatic alcohol are reacted with phosphorus sulfides to form aliphatic/aromatic phosphorodithioic acids. By the term aliphatic/aromatic, it is meant that either an aliphatic alcohol, an aromatic alcohol, or both, that is mixtures of both, can be used. Thus, the result approximates a statistical mixture of phosphorodithioic acids having only the aliphatic groups therein, only aromatic groups therein, or an aliphatic group and a aromatic group therein. With regard to the aromatic component of the acid, it generally can be naphthyl with phenyl being preferred. By the term (B) aromatic alcohol it is meant phenol, a low hydrocarbyl arene alcohol, or mixtures thereof.

By the term "hydrocarbyl substituent" or "hydrocarbyl group" it is meant a group as defined hereinabove. That is, a group of carbon atoms which are directly attached to the remainder of the molecule and have a predominately hydrocarbon character within the context of this invention. Specific examples of the various types of such hydrocarbyl groups are set forth hereinabove and thus are not repeated but hereby are fully incorporated by reference.

The (H) aliphatic alcohol can be unsaturated or desirably saturated, that is alkyl. Although linear or straight-chained aliphatics can be utilized, branched aliphatics are desirable in that they impart better solubility to the end product. The aliphatic alcohol can contain from 3 to about 22 carbon atoms, desirably from 4 to about 14 carbon atoms and preferably from about 5 to about 12 carbon atoms. Examples of specific aliphatic alcohols include propyl alcohol, butyl alcohol, amyl alcohol, hexyl alcohol, cyclohexyl alcohol, heptyl alcohol, octyl alcohol, nonyl alcohol, decyl alcohol, dodecyl alcohol, butyldecyl alcohol, octadecyl alcohol, oleyl alcohol, behenyl alcohol, euricic alcohol, tallow alcohol, as well as the various isomers thereof.

The amount of the aliphatic alcohols which are reacted with phosphorodithioic acids is generally from about 5 to about 90 percent equivalents, desirably from about 10 to about 75 percent equivalents with from about 15 to about 60 percent equivalents being preferred, and about 15 to about 50 equivalents being more preferred and about 20 to about 30 equivalents most preferred based upon 100 percent equivalents of said (H) aliphatic alcohols and the (B) aromatic alcohols.

The (B) aromatic alcohols such as low hydrocarbyl arene alcohols, phenol and combinations thereof, are generally the same as set forth above and hence will not be discussed in detail, but rather are hereby fully incorporated by reference. That is, the low hydrocarbyl arene alcohol has a total of usually 4 carbon atoms or less exclusive of the aromatic ring. In other words, since the number of variable carbon atoms are in the hydrocarbyl group(s) attached to the aromatic ring, such alcohols are conveniently discussed

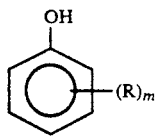

wherein $(R)_m$ can be suitable hydrocarbyl group(s), desirably an alkyl group(s) having from 0 to 4 carbon atoms, desirably from 1 to 4 carbon atoms with from 1 to 3 carbon atoms being preferred. The number of such R group(s), that is m is an integer of from 1 to 3 with 1 or 2 being preferred. When R is 0 carbon atoms, the aromatic alcohol is phenol. When R is 1 or more carbon atoms, a low hydrocarbyl arene alcohols exists. Oftentimes, a mixture of phenols and the low hydrocarbyl arene alcohols are used. A suitable class of compounds falling within the above formulation are generally referred to as the cresylic acids. Examples of specific types of cresylic acids or other aromatic alcohols are set forth hereinabove and hence are hereby full incorporated by reference. Inasmuch as such cresylic acids are derived from various fossil fuels and depend upon the particular type of fossil fuel and/or as well as the region of the world from which they are obtained, the content or "make-up" thereof can very greatly.

Since mixtures of the low hydrocarbyl arene alcohols are often utilized, for example, cresylic acids, the number of carbon atoms in the hydrocarbyl group $(R)_m$, often is not an integer. Accordingly, an overall average of carbon atoms is utilized. Thus, the low hydrocarbyl substituent (R) can contain an overall average number of carbon atoms of from 0.0 to about 4 carbon atoms, desirably from about 0.0 or 0.1 to about 3.5 carbon atoms and preferably from about 0.1 or 2.0 to about 3.0 carbon atoms.

The amount of the (B) aromatic alcohols is generally from about 10 to about 95 percent equivalents, desirably from about 25 percent to about 90 percent and preferably from about 40 percent to about 85 percent more preferably about 50 to about 85 percent and most preferably about 70 to about 80 percent equivalents based upon the total number of equivalents of both the (H) aliphatic alcohols and the (B) aromatic alcohols.

The acids of the present invention are generally prepared by reacting a solution containing a combination of both the (B) aromatic alcohols as well as the (H) aliphatic alcohols, in a ratio as set forth above, with various types of phosphorus sulfides. When necessary, non-phosphorus containing sulfur compounds can be utilized. Examples of various phosphorus sulfides include $P_2S_3$, $P_2S_5$, $P_4S_3$, $P_4S_7$. Examples of optional sulfur compounds include sulfur and sulfurized olefins as having from about 3 to 30, desirably 3 to 16, and often 8 carbon atoms or less. In the preparation of the acids, the phosphorus sulfides are initially reacted with the mixture of the aliphatic alcohols and the aromatic alcohols and then optionally reacted with the phosphorus-free sulfur compounds. Another procedure generally reacts only the aromatic alcohols with the phosphorus sulfides. Subsequently, the aliphatic alcohols can then be reacted. An amount of aliphatic alcohol is utilized as set forth above inasmuch as they will generally replace the aromatic alcohol substituent. The subsequent reaction of the aliphatic alcohols can be utilized either with regard to the free acid or the metal salts thereof. In any event, the optional phosphorus-free compounds can be reacted with any of the alcoholic products and generally in any stage of preparation thereof. Vacuum can then be applied to remove the displaced aromatic alcohols. Of the various phosphorus sulfur compounds, phosphorus pentasulfide is preferred.

The preparation of the desired phosphorodithioic acids including the relative amounts, for example, from about 3 to about 5 moles of alcohol per mole of phosphorus sulfur compound, and reaction temperature is as set forth above and accordingly is hereby incorporated by reference. Similarly, the reaction of the metal salts with the phosphorodithioic acids is also as set forth above and accordingly is hereby incorporated by reference including the reaction temperature, that is from about 30° C. to about 90° C. and avoiding any hydrolysis. Desirably, the metal salt formation is carried out in the presence of the diluent oil of low viscosity, for example about 3 to 7 centistokes at 40° C.

Although not being limited thereby, the formulation of the desired reaction product of the present embodiment is thought to be

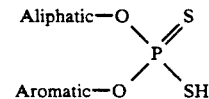

where (H) aliphatic and (B) aromatic are as defined above. Since mixtures of the aliphatic alcohol and the aromatic alcohol are used as set forth above, a statistical mixture results with acids as set forth above, or containing two (H) aliphatic groups or two (B) aromatic groups.

In utilizing a mixture of the aliphatic alcohol and the aromatic alcohol, various promoters can be utilized such as conventional amine promoters, for example alkylamine, cycloalkylamine, heterocyclicamine and the like. Examples of specific promoters include caprolactam, aniline, pyridine, and the like usually in the amount from about 0.0 to about 5.0 percent by weight based upon the total weight of the reactants. However, an important aspect of this invention is that the use of these or other promoters can generally be eliminated in that they are not always required.

Metal salts are generally desired which are neutral or basic and thus during the formation of the salt, an equivalent or a slight excess of the metal or the basic metal compound is utilized to yield such an end product. Accordingly, the amount of metal or basic metal compound utilized is an excess of about 0 to about 20 percent with an excess of about 5 percent to about 15 percent equivalents being desirable.

The types of various metals, basic metal compounds such as oxides, acetates, etc., suitable for use in the present invention are as set forth above and hereby full incorporated by reference. Zinc and copper, or combinations thereof are preferred.

The metal salt mixtures of the present invention not only impart good anti-wear properties to various organic diluents, but also tend to yield low viscosity products. In view of the fact that one of the alcoholic reactants is an aromatic alcohol which yields phosphorodithioics usually having poor anti-wear results, the fact that good anti-wear results were obtained was clearly unexpected.

The invention will be better understood by reference to the following examples listing the preparation of phosphorodithioic acids and metal salts thereof. All parts and percentages are by weight unless otherwise indicated.

EXAMPLE IA

A mixture of 246 parts (2 equivalents) of Cresylic Acid 33, 260 parts (2 equivalents) of isooctyl alcohol and 14 parts of caprolactam is heated to 55° C. under a nitrogen atmosphere. Phosphorus pentasulfide (222 parts, 2 equivalents) is added in portions over a 1 hour period while maintaining the temperature at about 78° C. The mixture is maintained at this temperature for an additional 1 hour until completion of the phosphorus pentasulfide addition and then cooled to room temperature. The reaction mixture is filtered and the filtrate is the desired phosphorodithioic acid.

EXAMPLE IB

Zinc oxide (44.8 parts, 1.1 equivalents), 102 parts of mineral oil and 7.5 parts of water are charged to a 1 liter flask. The phosphorodithioic acid (376 parts, 1.0 equivalents) prepared in Example IA is added over a 1.5 hour period with the reaction temperature allowed to increase from room temperature to about 50° C. After the addition of phosphorodithioic acid is complete, the temperature is raised to about 75° C. and held at that temperature for 3 hours. A vacuum is applied and the temperature is raised to about 100° C. The residue is filtered and the filtrate is the desired product. The product contains 6.39% P and 7.10% Zn.

EXAMPLE IIA

A mixture of 216 parts (2 equivalents) of p-cresol and 260 parts (2 equivalents) of isooctyl alcohol and 9.5 parts of caprolactam is heated to about 80° C. under a nitrogen atmosphere. Phosphorus pentasulfide (222 parts, 2 equivalents) is added in portions over a 1.5 hour period while maintaining the mixture at about 80°-85° C. The mixture is maintained at this temperature for 3.5 hours after the addition of phosphorus pentasulfide is complete and then cooled to room temperature. The reaction mixture is filtered and the filtrate is the desired phosphorodithioic acid.

EXAMPLE IIB

Zinc oxide (63 parts, 1.55 equivalents), 144 parts of mineral oil and 1 part of acetic acid are charged to a 3 liter flask. A vacuum is applied and 533 parts (1.3 equivalents) of the phosphorodithioic acid prepared in Example IIA are added while heating the mixture to about 80° C. The temperature is maintained at 80°-85° C. for 7 hours after addition of phosphorodithioic acid is complete. The residue is filtered and the filtrate is the desired product. The product contains 6.88% P.

EXAMPLE IIIA

A mixture of 394 parts (3.2 equivalents) of Cresylic Acid 33, 127 parts (0.8 equivalents) of decyl alcohol, and 14.2 parts of caprolactam is heated to about 75° C. under a nitrogen atmosphere. Phosphorus pentasulfide (222 parts, 2 equivalents) is added in portions over a 2 hour period at 75°-80° C. The mixture is maintained at this temperature for 1.5 hours after the addition of phosphorus pentasulfide is complete and then cooled to room temperature. The reaction mixture is filtered and the filtrate is the desired phosphorodithioic acid.

EXAMPLE IIIB

Zinc oxide (67 parts, 1.65 equivalents), and 160 parts of mineral oil are charged to a 1 liter flask. The phosphorodithioic acid (591 parts, 1.5 equivalents) prepared in Example IIIA is added while controlling the temperature at 40°-50° C. After the addition of phosphorodithioic acid is complete, the mixture is heated at about 75° C. for 3 hours. Vacuum is applied and the temperature of the mixture is increased to 105° C. The residue is filtered and the filtrate is the desired product. The product contains 13.5% S and 6.97% Zn.

EXAMPLE IVA

A mixture of 344 parts (2.8 equivalents) of Cresylic Acid 57 and 190 parts (1.2 equivalents) of decyl alcohol is heated to about 100° C. under a nitrogen atmosphere. Phosphorus pentasulfide (222 parts, 2 equivalents) is added in portions at 105°-115° C. After the addition is complete, the temperature is held at about 110° C. for 1.5 hours and then lowered to room temperature. The reaction mixture is filtered and the filtrate is the desired phosphorodithioic acid.

EXAMPLE IVB

Zinc oxide (67 parts, 1.65 equivalents) and 151 parts of mineral oil are charged to a 2 liter flask. The phosphordithioic acid (558 parts, 1.5 equivalents) prepared in Example IVA is added over a 2 hour period while controlling the temperature at about 50° C. After the addition of phosphorodithioic acid is complete, the temperature is raised to about 75° C. and maintained for 1.5 hours. A vacuum is applied and the temperature is increased to 100° C. The residue is filtered and the filtrate is the product. The product contains 12.7% S and 7.15% Zn.

EXAMPLE VA

Phenol (376 parts, 4 equivalents) is heated to about 150° C. under a nitrogen atmosphere. Phosphorus pentasulfide (222 parts, 2 equivalents) is added in portions. After the addition is complete, the temperature is held at about 150° C. for 1 hour. The mixture is cooled to 90° C. and 260 parts (2.0 equivalents) of isooctyl alcohol is added over a 2 hour period. After the alcohol addition is complete, the temperature is held at about 90° C. for 1 hour. A vacuum is applied and the temperature is increased to 120° C. The residue is filtered and the filtrate is the desired phosphorodithioic acid.

EXAMPLE VB

Zinc oxide (46 parts, 1.12 equivalents), 1 part of acetic acid, and 80 parts of mineral oil are charged to a 1 liter flask. A vacuum is applied and 320 parts (0.93 equivalents) of the phosphorodithioic acid prepared in Example VA is added over a 1 hour period at 50° C. After the addition is complete, the temperature is increased to about 80° C. and held for 3 hours. The residue is filtered and the filtrate is the product. The product contains 7.01% P and 7.41% Zn.

EXAMPLE VIA

A mixture of 260 parts (2 equivalents) of isooctyl alcohol, 188 parts (2 equivalents) of phenol, and 8.9 parts of caprolactam is heated to about 80° C. under a nitrogen atmosphere. Over a 1 hour period, 222 parts (2 equivalents) of phosphorus pentasulfide are added in portions. After the addition is complete, the temperature is held at 75°–80° C. for 2 hours and then lowered to room temperature. The reaction mixture is filtered and the filtrate is the desired phosphorodithioic acid.

EXAMPLE VIB

Zinc oxide (69 parts, 1.69 equivalents), 1 part of acetic acid, and 146 parts of mineral oil are charged to a 2 liter flask. A vacuum is applied and 539 parts (1.4 equivalents) of the phosphorodithioic acid prepared in Example VIA are added while heating the mixture to about 80° C. After the addition is complete, the temperature is held at about 80° C. for 4 hours. The residue is filtered and the filtrate is the desired product. The product contains 7.12% P and 14.05% S.

The products of the various examples contained in a fully formulated lubricating composition were then tested with regard to a Timken "OK" Load Test as well as a contact pressure test in accordance with ASTM D 2782 in the manner set forth hereinabove which is hereby fully incorporated by reference. The results of the various dithiophosphate salts according to the present invention are set forth in Table V.

TABLE V

TIMKEN EVALUATION OF MIXED AROMATIC/ ALIPHATIC ZINC DIOTHIOPHOSPHATES AT 0.05% P

| Example | Alcohol, Phenol Mixture (Mole %) | OK Value (lbs) | Contact Pressure (p.s.i.) |
|---|---|---|---|
| IB | 50% Cresylic Acid 33 50% Isooctyl Alcohol | 20 | 8,125 |
| IIIB | 80% Cresylic Acid 33 20% Decyl Alcohol | 23 | 10,150 |
| IVB | 70% Cresylic Acid 57 30% Decyl Alcohol | 20 | 12,700 |
| — | 100% Heptylphenol | 13 | 7,750 |
| — | 100% Isooctyl Alcohol | 15 | 5,075 |
| VIB | 50% Phenol 50% Isooctyl Alcohol | 20 | 8,696 |

It is apparent from Table V, Examples IB, IIIB, IVB and VIB made according to the present invention had good "OK" load test values as well as good contact pressures. In contrast thereto, a composition containing only aliphatic phosphorodithioic acid salts had poor values. The fact that the aliphatic containing salt had poor values is a clear indication that the result obtained with a metal salt thereof containing an aromatic as well as an aliphatic group was unexpected.

As previously noted, the compositions of the present invention are useful as additives for lubricants and functional fluids. They can be employed in a variety of lubricants based on diverse oils of lubricating viscosity, including natural and synthetic lubricating oils and mixtures thereof. The lubricants include crankcase lubricating oils for spark-ignited and compression-ignited internal combustion engines, including automobile and truck engines, two-cycle engines, aviation piston engines, marine and railroad diesel engines, and the like. Also contemplated are lubricants for gas engines, stationary power engines and turbines and the like. Transaxle lubricants, gear lubricants, metal-working lubricants and other lubricating oil and grease compositions, as well as functional fluids such as hydraulic fluids and automatic transmission fluids, benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale oil can also be included as the base oil.

Synthetic lubricating oils include hydrocarbon oils and halo-substituted hydrocarbon oils such as polymerized and interpolymerized olefins (e.g., polybutylenes, polypropylenes, propylene-isobutylene, copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di(2-ethylhexyl) benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g. methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di-(2-ethylhexyl) sebacate, di-n-hexyl fumarate, dioctyl sebacate, diisooctyl azelate, diisodecyl acelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another class of synthetic oils (e.g., tetraethyl silicate, tetraisopropyl silicate, tetra-(p-tertbutylphenyl) silicate, hexa-(4-methyl-2-pentoxy)-disiloxane, poly(methyl) siloxanes, poly (methylphenyl)siloxanes, etc.). Other synthetic oils include liquid esters of phosphorus-containing acids (e.g., tricresyl phosphate, trioctyl phosphate, diethyl ester of decylphosphonic acid, tc.), polymeric tetra-hydrofurans and the like.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or an ester oil obtained directly from an esterification process and used without further treatment would be an unrefined oil. Refined oils are similar to the unrefined oils except they have been further treatment in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already in service. Such rerefined oils are also known as reclaimed or reprocessed oils and often are additionally processed by techniques directed to removal of spent additives and oil breakdown products.

Generally, the lubricants and functional fluids of the present invention contain an amount of the compositions of this invention sufficient to provide it with anti-oxidant and/or anti-wear properties. Normally this amount will be about 0.25 percent to about 10 percent, preferably about 0.4 percent to about 7.5 percent of the total weight of the fluid.

The invention also contemplates the use of other additives in combination with the compositions of this invention. Such additives include, for example, detergents and dispersants of the ash-producing or ashless type, corrosion- and auxiliary oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-betanaphthylamine, and dodecylamine. A particularly effective method for preparing the basic salts comprises mixing an acid with an excess of a basic alkaline earth metal neutralizing agent and a least one alcohol promoter, and carbonating the mixture at an elevated temperature such as 60°-200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products are carboxylic acids (or derivatives thereof) containing at least about 34 and preferably at least about 54 carbon atoms with nitrogen- containing compounds such as amine, organic hydroxy compounds such as phenols and alcohols, and/or basic inorganic materials. Examples of these "carboxylic dispersants" are described in British Patent 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamides. These may be characterized as "amine dispersants" and examples thereof are described for example, in the following U.S. patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |

| | -continued | | |
|---|---|---|---|
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. patents:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Auxiliary extreme pressure agents and corrosion- and auxiliary oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; and metal dithiocarbamates, such as zinc dioctyldithiocarbamate and barium heptylphenyl dithiocarbamate.

Pour point depressants are a particularly useful type of additive often included in the lubricating oils described herein. The use of such pour point depressants in oil-based composition to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates, polyacrylates; polyacrylamides; condensation products of haloparaffin waxes and aromatic compounds, vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; and 3,250,715 which are hereby incorporated by reference for their relevant disclosures.

The metal salt compositions of this invention can be added directly to the lubricant. When contained in a lubricant composition, the amount of the metal salt compositions is such that the amount of phosphorus in said lubricating composition from about 0.001 to about 0.15 parts by weight per 100 parts by weight of the lubricant composition. A more desirable amount of the metal salts of hydrocarbyl substituted aromatic phosphorodithioic acids or the hydrocarbyl substituted aromatic/aliphatic phosphorodithioic is from 0.025 to about 0.1 parts by weight of the phosphorus in said lubricant composition. However, they are often diluted with a substantially inert, normally liquid organic diluent such as mineral oil, naphtha, benzene, toluene, xylene, or the like to form an additive concentrate. These concentrates usually contain from about 3 to about 90 percent by weight of the metal salts of the present invention, as set forth in Table VI. Additionally, the concentrates can contain one or more additive known in the art or described hereinabove. The remainder of the concentrate is substantially inert normally liquid diluent.

The amount of the metal salts contained in the lubricant composition is generally a minor amount with a major amount being the lubricating oil.

TABLE VI

| Concentrate A | |
|---|---|
| Product of Example 1D | 34.5% by weight |
| Mineral Oil | 13.8% by weight |
| Basic Calcium Petroleum Sulfonate | 51.76% by weight |
| Concentrate B | |
| Product of Example 1B | 10% by weight |
| Mineral Oil | 90% by weight |
| Concentrate C | |
| Product of Example 2B | 15% by weight |
| Mineral Oil | 50% by weight |
| Polybutenyl Succinic Anydride-Ethylene Polyamine Reaction Product | 35% by weight |

Similarly, concentrates were made containing the hydrocarbyl substituted aromatic/aliphatic phosphorodithioic acid salts of the present invention and are set forth in Table VII.

TABLE VII

| Concentrate A | |
|---|---|
| Product of Example IB | 10% by weight |
| Mineral Oil | 90% by weight |
| Concentrate B | |
| Product of Example VB | 15% by weight |
| Basic Calcium Petroleum Sulfonate | 15% by weight |
| Polybutenyl Succinic Anhydride-Ethylene Polyamine Reaction Product | 25% by weight |
| Mineral Oil | 45% by weight |
| Concentrate C | |
| Product of Example IVB | 10% by weight |
| Basic Sodium Petroleum Sulfonate | 15% by weight |
| Basic Magnesium Petroleum Sulfonate | 15% by weight |
| Reacton Product of Polybutenyl Succinic Anhydride with Ethylene Polyamine and Pentaerythritol | 25% by weight |
| Mineral Oil | 35% by weight |

These concentrates have good solubility with regard to the metal salts therein.

While in accordance with the patent statutes a best mode and preferred embodiment have been set forth, it is to be understood that various modifications thereof will become apparent to those skilled in the art upon reading of the specification. Therefore, it is to be understood that the invention disclosed herein is intended to cover such modifications as fall within the scope of the attached claims.

What is claimed is:

1. A lubricating composition, comprising a major amount of an oil of lubricating viscosity and a minor amount of a mixture of metal salts of phosphorodithioic acids prepared by the reaction of a metal or basic metal compound; a phosphorus sulfide; and (I) a mixture of low hydrocarbyl arene alcohols represented by the following formula (B):

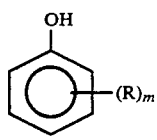

(B)

wherein (R) is a low hydrocarbyl group having from 1 to 4 carbon atoms and m is a number from 0-3 such that the low hydrocarbyl group (R) contains an overall average number of from 0.1 to about 3.5 carbon atoms in the mixture of low hydrocarbyl arene alcohols; and (II) at least one aliphatic alcohol (H) containing from 3 to about 22 carbon atoms;

wherein the mixture of low hydrocarbyl arene alcohols is present in an amount of from about 50% to about 85% equivalents and the aliphatic alcohol (H) is present in an amount from about 15% to about 50% equivalents based on the total equivalents of (B) and (H).

2. The composition as claimed in claim 1 wherein the aromatic group has an average carbon substituent from about 0 to about 4 carbon atoms and the aliphatic group is an alkyl group containing from about 4 to about 14 carbon atoms.

3. The composition claimed in claim 1 wherein the metal is selected from the group consisting of zinc, copper, nickel, cobalt, iron, potassium, tin, sodium, calcium, and combinations thereof.

4. The composition as claimed in claim 1, wherein the aromatic group has an average carbon substituent of from 2 to about 3 carbon atoms and wherein the metal is zinc.

5. The lubricating composition of claim 1 wherein the low hydrocarbyl arene alcohol (B) is present in an amount from about 70% to about 80% equivalents and the aliphatic alcohol (H) is present in an amount from about 20% to about 30% equivalents based on the total equivalents of (B) and (H).

6. A concentrate, comprising:
a liquid organic diluent and from about 3 to about 90 percent by weight of a mixture of metal salts of phosphorodithioic acids prepared by the reaction of a metal or basic metal compound; a phosphorus sulfide; and (I) a mixture of low hydrocarbyl arene alcohols represented by the following formula (B):

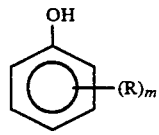

(B)

wherein (R) is a low hydrocarbyl group having from 1 to 4 carbon atoms and m is a number from 0-3 such that the low hydrocarbyl group (R) contains an overall average number of from 0.1 to about 3.5 carbon atoms in the mixture of low hydrocarbyl arene alcohols; and (II) at least one aliphatic alcohol (H) containing from 3 to about 22 carbon atoms; wherein the mixture of low hydrocarbyl arene alcohols is present in an amount of from about 50% to about 85% equivalents and the aliphatic alcohol (H) is present in an amount from about 15% to about 50% equivalents based on the total equivalents of (B) and (H).

7. The concentrate of claim 6 wherein the low hydrocarbyl arene alcohol (B) is present in an amount from about 70% to about 80% equivalents and the aliphatic alcohol (H) is present in an amount from about 20% to about 30% equivalents based on the total equivalents of (B) and (H).

* * * * *